(12) United States Patent
Hsieh

(10) Patent No.: US 6,285,732 B1
(45) Date of Patent: Sep. 4, 2001

(54) METHODS AND APPARATUS FOR ADAPTIVE INTERPOLATION REDUCED VIEW CT SCAN

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/440,733

(22) Filed: Nov. 16, 1999

(51) Int. Cl.$^7$ ........................................................ A61B 6/03
(52) U.S. Cl. .................................................. 378/4; 378/901
(58) Field of Search ........................... 378/4, 15, 19, 378/901

(56) References Cited

U.S. PATENT DOCUMENTS 5,828,718 * 10/1998 Ruth et al. ............................. 378/19
5,848,117 * 12/1998 Urchuk et al. ......................... 378/19
5,946,371 * 8/1999 Lai ......................................... 378/19

* cited by examiner

*Primary Examiner*—David V. Bruce
(74) *Attorney, Agent, or Firm*—Armstrong Teasdale LLP; Christian G. Cabou

(57) ABSTRACT

In one aspect, the present invention is a method for computerized tomographic (CT) imaging of an object, the method including steps of scanning an object with a CT imaging system to acquire views including projection samples of an object; interpolating the views nonuniformly within a selected view range to produce nonuniformly interpolated views; weighting the views, including weighting the acquired views and the nonuniformly interpolated views, to compensate for the nonuniform interpolation; and filtering and backprojecting the views to generate an image of the object.

Improved CT imaging is thus provided by reducing view aliasing artifacts without simultaneously reducing spatial resolution to clinically unacceptable levels.

22 Claims, 1 Drawing Sheet

METHODS AND APPARATUS FOR ADAPTIVE INTERPOLATION REDUCED VIEW CT SCAN

BACKGROUND OF THE INVENTION

This invention relates to tomographic imaging, and more particularly to methods and apparatus for reducing aliasing artifacts in computerized tomographic imaging.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT imaging system is available that combines a gantry rotation rate of 0.8 s with a data acquisition system (DAS) sampling rate of 1230 Hz. As a result, a projection sampling rate of 984 views per gantry rotation. Theoretical, experimental, and clinical investigations have shown that, from a standpoint of aliasing, this sampling rate is near a lower limit. It would be desirable to increase the scan rate to at least 0.5 s per gantry rotation to reduce motion artifacts and to reduce imaging times, but to do so would require a higher sampling rate. Hardware limitations limit maximum sampling rates, however. For example, hardware and software limitations may limit a DAS sampling rate to 1408 Hz. For a 0.5 s scan, 704 views per gantry rotation would be obtained in such a system, a 28.5% reduction compared to systems providing 984 views per gantry rotation. If proper compensation is not performed, view aliasing artifacts, such as streaks, will result. Such aliasing artifacts are known to be quite objectionable to radiologists.

Because the artifacts result from reduction of view sampling, it would seem logical to try to increase a number of views in a reconstruction with interpolation in a view direction. For example, a 2:1 view expansion of an acquired data set could be attempted to increase a number of acquired views from 704 to 1408. This approach, however, leads to significant reduction in spatial resolution, because view interpolation is typically a low-pass filtering process. Phantom experiments indicate that the degradation in spatial resolution can reach clinically unacceptable levels.

It would therefore be desirable to provide methods and apparatus for CT imaging with reduction of view aliasing artifacts without clinically unacceptable reduction in spatial resolution.

BRIEF SUMMARY OF THE INVENTION

Therefore, in one embodiment of the present invention, there is provided a method for computerized tomographic (CT) imaging of an object, the method including steps of scanning an object with a CT imaging system to acquire views including projection samples of an object; interpolating the views nonuniformly within a selected view range to produce nonuniformly interpolated views; weighting the views, including weighting the acquired views and the nonuniformly interpolated views, to compensate for the nonuniform interpolation; and filtering and backprojecting the views to generate an image of the object.

Improved CT imaging is thus provided, in this embodiment, by reducing view aliasing artifacts without simultaneously reducing spatial resolution to clinically unacceptable levels.

DETAILED DESCRIPTION OF THE INVENTION

Figure 1:
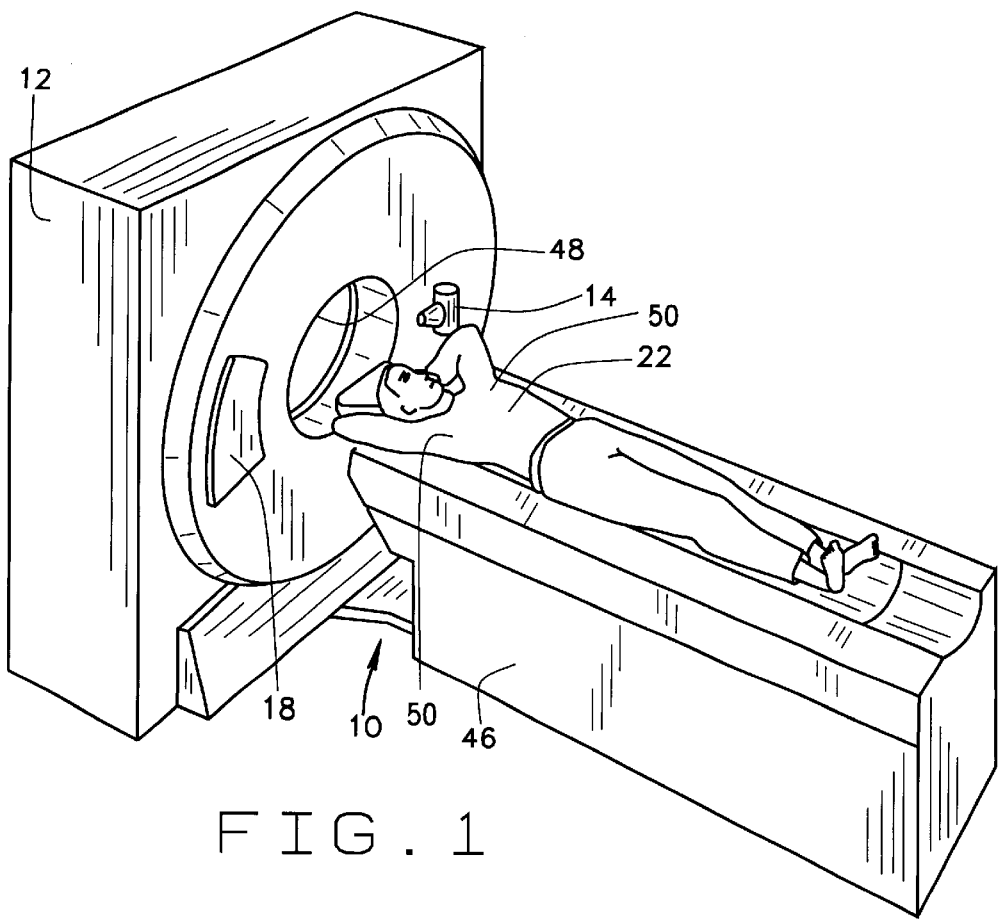
FIG. 1 is a pictorial view of a CT imaging system.
Figure 2:
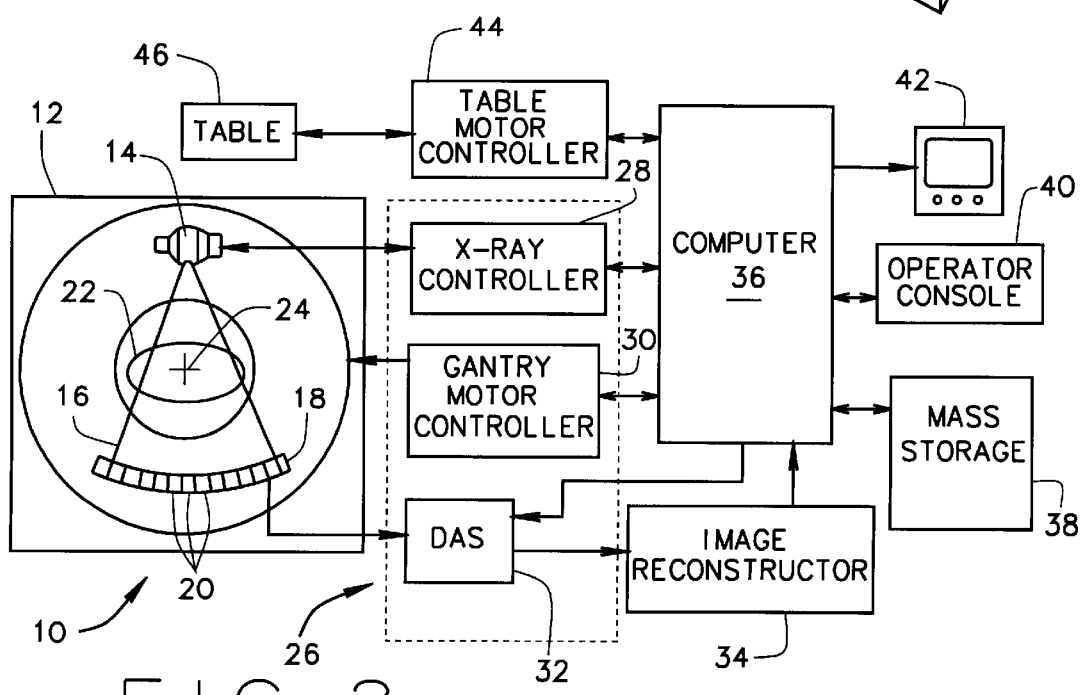
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

A majority of clinical aliasing artifacts occur when a dense object is located near an outer region of a field of view, because the view requirement is roughly proportional to the distance of an object from the CT isocenter. In human anatomy, dense objects causing aliasing are predominantly oriented in a horizontal direction. For example, shoulder bones 50 of patient 22, which are typically oriented horizontally when patient 22 is scanned, often produce aliasing streaks. It is desirable to provide a maximum of aliasing reduction in a direction in which aliasing occurs most often, and a minimum of aliasing reduction in a direction in which aliasing occurs less frequently. Such an aliasing reduction configuration provides a good compromise between aliasing artifact reduction and reduction of spatial resolution.

Thus, in one embodiment of the present invention, an object 22, for example, a patient, is scanned with CT imaging system 10 to acquire views comprising projection samples of the object 22. These views are further processed by image reconstructor 34 into images that are stored by computer 36 in storage device 38 for viewing on CRT display 42. (Because design choices are available in which distributed processing of images in various CT imaging systems 10 is performed, it will be understood that the invention is not limited to embodiments in which all processing is performed by a discrete image reconstructor 34.) This processing includes steps of interpolating views of the object nonuniformly within a selected view range to produce nonuniformly interpolated views; weighting the views, including weighting the nonuniformly interpolated views and the acquired views, to compensate for the nonuniform interpolation; and filtering and backprojecting the views to generate an image of the object.

View interpolation is carried out in a view range of $[0.5\pi-\beta_0\beta_1, 0.5\pi+\beta_0+\beta_1]$ and $[1.5\pi-\beta_0-\beta_1, 1.5\pi+\beta_0+\beta_1]$, where $\beta_0$ and $\beta_1$ are parameters. In one embodiment, parameters, $\beta_0$ and $\beta_1$ are both equal to 0.357 radians (20.45°) and are modifiable during clinical stages. Many view interpolation schemes are suitable. For example, a general Lagrange interpolation is used in one embodiment. A set of projection samples $p(\gamma,\beta_i)$, where $\gamma$ is a projection fan angle, is located at view angles $\beta_i$, where $i=1,\ldots,N$ and N is the number of view angles in the set. An estimated projection $p'(\gamma,\beta)$ at location, $\beta$ is written as:

$$p'(\gamma,\beta) = \sum_{i=1}^{N} \xi p(\gamma,\beta_i),$$

where:

$$\xi = \frac{\prod_{\forall k \neq i}(\beta - \beta_k)}{\prod_{\forall k \neq i}(\beta_i - \beta_k)}.$$

A Lagrange interpolator, for example, a fourth-order Lagrange interpolator used in one embodiment, advantageously preserves original data samples when $\beta=\beta_i$. To avoid streak artifacts resulting from sharp transitions near boundaries of an interpolation range, interpolated views are weighted prior to the filtered backprojection process by a function $w(\gamma,\beta)$ written as:

$$w(\gamma,\beta) = \begin{cases} \alpha(3\theta^2 - 2\theta^3) & \beta_c - \beta_0 - \beta_1 \leq \beta < \beta_c - \beta_0 \\ \alpha & \beta_c - \beta_0 \leq \beta \leq \beta_c + \beta_0 \\ \alpha - \alpha(3\psi^2 - 2\psi^3) & \beta_c + \beta_0 < \beta < \beta_c + \beta_0 + \beta_1 \end{cases}$$

where $\beta_c=0.5\pi$ or $\beta_c=1.5\pi$, and is dependent on the interpolated projection region;

$\alpha$ is a parameter, which in one embodiment, is equal to 0.25;

$$\theta = \frac{\beta - (\beta_c - \beta_0 - \beta_1)}{\beta_1}; \text{ and}$$

$$\psi = \frac{\beta - (\beta_c + \beta_0)}{\beta_1}.$$

Because projection samples are not interpolated uniformly across a range of $2\pi$, the ray sampling pattern is no longer homogeneous. More specifically, for each ray path, a sampling density is increased in regions in which interpolation takes place. Therefore, proper compensation is provided to reduce shading artifacts.

To compensate for non-homogenous sampling, conjugate sampling pairs present in a fan beam geometry are used. For a $2\pi$ projection angle, two samples $(\gamma,\beta)$ and $(-\gamma,\beta+\pi-2\gamma)$ are redundant in that they represent samples taken with identical ray paths. By providing proper weights to conjugated samples of interpolated views, an overall contribution from all samples can be kept constant. More specifically, the contribution of conjugate samples are reduced by a same amount to ensure that overall homogeneity is preserved. Acquired projections are weighted by a function $w(\gamma,\beta)$ prior to the filtered backprojection. For ease of reference, let $\Gamma$ denote a region in which $w'(\gamma,\beta)$ is applied. Outside $\Gamma$, $w'(\gamma,\beta)=1$. Otherwise, $w'(\gamma,\beta)$ is written:

$$w'(\gamma,\beta) =$$

$$\begin{cases} 1 - \alpha(3\theta'^2 - 2\theta'^3) & \beta_c - \beta_0 - \beta_1 \pm \pi - 2\gamma \leq \beta < \beta_c - \beta_0 \pm \pi - 2\gamma \\ 1 - \alpha & \beta_c - \beta_0 \pm \pi - 2\gamma \leq \beta < \beta_c + \beta_0 \pm \pi - 2\gamma \\ 1 + \alpha(3\psi'^2 - 2\psi'^3 - 1) & \beta_c + \beta_0 \pm \pi - 2\gamma < \beta \leq \beta_c + \beta_0 + \beta_1 \pm \pi - 2\gamma \end{cases}$$

where $\beta_c=0.5\pi$ or $\beta_c=0.5\pi$, depending upon an interpolated projection region, $$\theta' = \frac{\beta - (\beta_c - \beta_0 - \beta_1 \pm \pi - 2\gamma)}{\beta_1} \text{ and}$$

$$\psi' = \frac{\beta - (\beta_c + \beta_0 \pm \pi - 2\gamma)}{\beta_1}.$$

For many clinical applications, additional weighting functions are applied to the projections to compensate for projection data inconsistency. For example, to compensate for patient motion, an under-scan weight is applied. For helical applications, helical-related weighting functions are applied to reduce helical artifacts. Thus, in one embodiment, the adaptive interpolation described above is used in conjunction with at least one other weighting function. Interpolated views are weighted in accordance with equation (2) and the appropriate additional helical or underscan weights. As a result, the interpolated views are weighted by w(γ,β) μ(γ,β), where μ(γ,β) is the appropriate helical or underscan weight. In another embodiment, interpolations are performed on helically weighted projections. The weighting w(γ,β) is then applied to the interpolated data. For a region defined by Γ, a weighting function of this embodiment is written as, μ(γ,β)−[1−μ(γ,β)][1−w'(γ,β)]. For regions outside of Γ, a helical weighting function μ(γ,β) is applied. This embodiment does not significantly impact reconstruction speed, because no additional filtering or backprojection are required.

From the preceding description of various embodiments of the present invention, it is evident that methods and apparatus of the present invention provide improved CT imaging by reducing view aliasing artifacts without simultaneously reducing spatial resolution to clinically unacceptable levels.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan. Accordingly, the spirit and scope of the invention are to be limited only by the terms of the appended claims and legal equivalents.

What is claimed is:

1. A method for computerized tomographic (CT) imaging of an object, said method comprising:
   scanning an object with a CT imaging system to acquire views comprising projection samples of an object;
   interpolating the views nonuniformly within a selected view range to produce nonuniformly interpolated views;
   weighting the views, including weighting the acquired views and the nonuniformly interpolated views, to compensate for the nonuniform interpolation; and
   filtering and backprojecting the views to generate an image of the object.

2. A method in accordance with claim 1 wherein interpolating views nonuniformly within a selected range comprises the step of interpolating views nonuniformly within a view range of [$0.5\pi - \beta_0 - \beta_1$, $0.5\pi + \beta_0 + \beta_1$] and [$1.5\pi - \beta_0 - \beta_1$, $1.5\pi + \beta_0 + \beta_1$], where $\beta_0$ and $\beta_1$ are parameters.

3. A method in accordance with claim 2 wherein $\beta_0 = \beta_1 = 0.357$ radians.

4. A method in accordance with claim 2 wherein the object is a patient and further comprising the step of modifying parameters $\beta_0$ and $\beta_1$ during a clinical stage of the patient.

5. A method in accordance with claim 2 wherein interpolating views nonuniformly within a selected view range comprises the step of applying a Lagrange interpolator to the projection samples of the object.

6. A method in accordance with claim 5 wherein applying a Lagrange interpolator to the projection samples of the object comprises the step of applying a fourth-order Lagrange interpolator to the projection samples of the object.

7. A method in accordance with claim 5 herein applying a Lagrange interpolator to the projection samples of the object comprises determining an estimated projection p'(γ,β) as:

$$p'(\gamma, \beta) = \sum_{i=1}^{N} \xi p(\gamma, \beta_i),$$

where:

$$\xi = \frac{\prod_{\forall k \neq i}(\beta - \beta_k)}{\prod_{\forall k \neq i}(\beta_i - \beta_k)};$$

p(γ,$\beta_i$) is a set of projection samples located at a view angle $\beta_i$, where i=1, ..., N, and N is the number of view angles in the set; and γ is a projection fan angle.

8. A method in accordance with claim 2 further comprising the step of weighting the Lagrange interpolated views to remove streak artifacts.

9. A method in accordance with claim 8 wherein weighting the Lagrange interpolated views to remove streak artifacts comprises weighting the Lagrange interpolated views with a function:

$$w(\gamma, \beta) = \begin{cases} \alpha(3\theta^2 - 2\theta^3) & \beta_c - \beta_0 - \beta_1 \leq \beta < \beta_c - \beta_0 \\ \alpha & \beta_c - \beta_0 \leq \beta \leq \beta_c + \beta_0 \\ \alpha - \alpha(3\psi^2 - 2\psi^3) & \beta_c + \beta_0 < \beta < \beta_c + \beta_0 + \beta_1 \end{cases}$$

where $\beta_c = 0.5\pi$ or $\beta_c = 1.5\pi$, dependent on the interpolated projection region;

α is a parameter, $$\theta = \frac{\beta - (\beta_c - \beta_0 - \beta_1)}{\beta_1}, \text{ and}$$

$$\psi = \frac{\beta - (\beta_c + \beta_0)}{\beta_1}.$$

10. A method in accordance with claim 9 wherein α=0.25.

11. A method in accordance with claim 2 wherein weighting the views comprises the step of weighting acquired projections with a function w'(γ,β) prior to filtering and backprojecting in a region Γ, where, outside Γ, w'(γ,β)=1, and inside Γ:

$$w'(\gamma, \beta) = \begin{cases} 1 - \alpha(3\theta'^2 - 2\theta'^3) & \beta_c - \beta_0 - \beta_1 \pm \pi - 2\gamma \leq \beta < \beta_c - \beta_0 \pm \pi - 2\gamma \\ 1 - \alpha & \beta_c - \beta_0 \pm \pi - 2\gamma \leq \beta < \beta_c + \beta_0 \pm \pi - 2\gamma \\ 1 + \alpha(3\psi'^2 - 2\psi'^3 - 1) & \beta_c + \beta_0 \pm \pi - 2\gamma < \beta \leq \beta_c + \beta_0 + \beta_1 \pm \pi - 2\gamma \end{cases}$$

where $\beta_c=0.5\pi$ or $\beta_c=0.5\pi$, depending upon an interpolated projection region, $$\theta' = \frac{\beta - (\beta_c - \beta_0 - \beta_1 \pm \pi - 2\gamma)}{\beta_1} \text{ and}$$

$$\psi' = \frac{\beta - (\beta_c + \beta_0 \pm \pi - 2\gamma)}{\beta_1}.$$

12. A computerized tomographic (CT) imaging system configured to:
  scan an object to acquire views comprising projection samples of the object;
  interpolate the views nonuniformly within a selected view range to obtain nonuniformly interpolated views;
  weight the views, including the nonuniformly interpolated views and the acquired views, to compensate for the nonuniform interpolation; and
  filter and backproject the views to generate an image of the object.

13. A CT imaging system in accordance with claim 12 wherein said system being configured to interpolate views nonuniformly within a selected range comprises said system being configured to interpolate views nonuniformly within a view range of [0.5π−β₀−β₁, 0.5π+β₀+β₁] and [1.5π−β₀−β₁, 1.5π+β₀+β₁], where β₀ and β₁ are parameters.

14. A CT imaging system in accordance with claim 13 wherein β₀=β₁=0.357 radians.

15. A CT imaging system in accordance with claim 13 further configured to image a patient, and to modify parameters β₀ and β₁ during a clinical stage of the patient.

16. A CT imaging system in accordance with claim 13 wherein said system being configured to interpolate views nonunifornly within a selected view range comprises said system being configured to apply a Lagrange interpolator to the projection samples of the object.

17. A CT imaging system in accordance with claim 16 wherein said system being configured to apply a Lagrange interpolator to the projection samples of the object comprises said system being configured to apply a fourth-order Lagrange interpolator to the projection samples of the object.

18. A CT imaging system in accordance with claim 16 herein said system being configured to apply a Lagrange interpolator to the projection samples of the object comprises said system being configured to determine an estimated projection p'(γ,β) as:

$$p'(\gamma, \beta) = \sum_{i=1}^{N} \xi p(\gamma, \beta_i),$$

where:

$$\xi = \frac{\prod_{\forall k \neq i} (\beta - \beta_k)}{\prod_{\forall k \neq i} (\beta_i - \beta_k)};$$

p(γ,β_i) is a set of projection samples located at a view angle β_i, where i=1, ..., N, and N is the number of view angles in the set; and γ is a projection fan angle.

19. A CT imaging system in accordance with claim 13 further configured to weight the Lagrange interpolated views to remove streak artifacts.

20. A CT imaging system in accordance with claim 19 wherein said system being configured to weight the Lagrange interpolated views to remove streak artifacts comprises said system being configured to weight the Lagrange interpolated views with a function:

$$w(\gamma, \beta) = \begin{cases} \alpha(3\theta^2 - 2\theta^3) & \beta_c - \beta_0 - \beta_1 \leq \beta < \beta_c - \beta_0 \\ \alpha & \beta_c - \beta_0 \leq \beta \leq \beta_c + \beta_0 \\ \alpha - \alpha(3\psi^2 - 2\psi^3) & \beta_c + \beta_0 < \beta < \beta_c + \beta_0 + \beta_1 \end{cases}$$

where $\beta_c=0.5\pi$ or $\beta_c=1.5\pi$, dependent on the interpolated projection region;

α is a parameter, $$\theta = \frac{\beta - (\beta_c - \beta_0 - \beta_1)}{\beta_1}, \text{ and}$$

$$\psi = \frac{\beta - (\beta_c + \beta_0)}{\beta_1}.$$

21. A CT imaging system in accordance with claim 20 wherein α=0.25.

22. A CT imaging system in accordance with claim 13 wherein said system being configured to weight the views comprises said system being configured to weight acquired projections with a function w'(γ,β) prior to filtering and backprojecting in a region Γ, where, outside Γ, w'(65 ,β)=1, and inside Γ:

$$w'(\gamma, \beta) = \begin{cases} 1 - \alpha(3\theta'^2 - 2\theta'^3) & \beta_c - \beta_0 - \beta_1 \pm \pi - 2\gamma \leq \beta < \beta_c - \beta_0 \pm \pi - 2\gamma \\ 1 - \alpha & \beta_c - \beta_0 \pm \pi - 2\gamma \leq \beta < \beta_c + \beta_0 \pm \pi - 2\gamma \\ 1 + \alpha(3\psi'^2 - 2\psi'^3 - 1) & \beta_c + \beta_0 \pm \pi - 2\gamma < \beta \leq \beta_c + \beta_0 + \beta_1 \pm \pi - 2\gamma \end{cases}$$

where $\beta_c=0.5\pi$ or $\beta_c=0.5\pi$, depending upon an interpolated projection region, $$\theta' = \frac{\beta - (\beta_c - \beta_0 - \beta_1 \pm \pi - 2\gamma)}{\beta_1} \text{ and}$$

$$\psi' = \frac{\beta - (\beta_c + \beta_0 \pm \pi - 2\gamma)}{\beta_1}.$$

* * * * *

UNITED STATES PATENT AND TRADEMARK OFFICE
CERTIFICATE OF CORRECTION

PATENT NO.        : 6,285,732 B1  
APPLICATION NO. : 09/440733  
DATED              : September 4, 2001  
INVENTOR(S)      : Hsieh It is certified that error appears in the above-identified patent and that said Letters Patent is hereby corrected as shown below:

In Specification, column 3, line 57, delete "$[0.5\pi\text{-}\beta_0\beta_1$" and insert therefore -- $[0.5\pi\text{-}\beta_0\text{-}\beta_1$ --.

In Specification, column 3, line 66, delete "location, $\beta$" and insert therefore -- location $\beta$ --.

In Specification, column 4, line 66, delete "or $\beta_c=0.5\pi$" and insert therefor -- or $\beta_c=1.5\pi$ --.

In Claim 11, column 7, line 20, delete "or $\beta_c=0.5\pi$" and insert therefor -- or $\beta_c=1.5\pi$ --.

In Claim 18, column 7, line 66, delete "herein" and insert therefor -- wherein --.

In Claim 22, column 8, line 56, delete bolded "65" and insert therefor -- $y$ --.

In Claim 22, column 9, line 1, delete "or $\beta_c=0.5\pi$" and insert therefor -- or $\beta_c=1.5\pi$ --.

Signed and Sealed this

Seventeenth Day of July, 2007

JON W. DUDAS  
*Director of the United States Patent and Trademark Office*